(12) United States Patent
Baumann et al.

(10) Patent No.: US 9,668,660 B2
(45) Date of Patent: Jun. 6, 2017

(54) ACTIVE MEDICAL DEVICE FOR MONITORING THE STATUS OF A PATIENT SUFFERING FROM A RISK OF HEART FAILURE

(71) Applicant: SORIN CRM SAS, Clamart (FR)

(72) Inventors: Oliver Baumann, Southampton (GB); Lionel Giorgis, Saint Brieuc (FR)

(73) Assignee: SORIN CRM SAS, Clamart (FR)

( * ) Notice: Subject to any disclaimer, the term of this patent is extended or adjusted under 35 U.S.C. 154(b) by 0 days.

(21) Appl. No.: 14/997,303

(22) Filed: Jan. 15, 2016

(65) Prior Publication Data
US 2016/0128581 A1    May 12, 2016

Related U.S. Application Data

(62) Division of application No. 13/941,123, filed on Jul. 12, 2013, now Pat. No. 9,247,888.

(30) Foreign Application Priority Data

Jul. 13, 2012 (FR) .................... 12 56792

(51) Int. Cl.
*A61B 5/0255* (2006.01)
*A61B 5/00* (2006.01)
(Continued)

(52) U.S. Cl.
CPC ............ *A61B 5/0255* (2013.01); *A61B 5/024* (2013.01); *A61B 5/02028* (2013.01);
(Continued)

(58) Field of Classification Search
CPC . A61B 5/02028; A61B 5/024; A61B 5/02405; A61B 5/0245; A61B 5/0255;
(Continued)

(56) References Cited

U.S. PATENT DOCUMENTS 4,669,485 A  *  6/1987  Russell ................. A61B 5/021
                                                          600/492
4,718,426 A  *  1/1988  Russell ................. A61B 5/021
                                                          600/490
(Continued)

FOREIGN PATENT DOCUMENTS

EP      0 347 708         12/1989
EP      0 515 319 A1      11/1992
(Continued)

OTHER PUBLICATIONS

Preliminary Search Report for French Patent Application No. 1256792, dated Mar. 19, 2013, 3 pages.

*Primary Examiner* — Christopher A Flory
(74) *Attorney, Agent, or Firm* — Foley & Lardner LLP

(57) ABSTRACT

An active medical device is configured to receive inputs and to calculate a hemodynamic parameter representative of myocardium contractility determined from an endocardial acceleration signal. The microcontroller acquires heart rate and hemodynamic parameter pairs of values during a plurality of cardiac cycles. The microcontroller is configured to distribute the pairs of values into discrete bins to develop a profile for analysis. The microcontroller is configured to conduct an analysis comprising calculating an index representative of the patient's clinical status. The hemodynamic parameter representative of the myocardial contractility is a time interval separating the first and the second peak of endocardial acceleration.

19 Claims, 3 Drawing Sheets

(51) Int. Cl.
*A61B 5/02* (2006.01)
*A61B 5/024* (2006.01)

(52) U.S. Cl.
CPC .......... *A61B 5/6869* (2013.01); *A61B 5/7275* (2013.01); *A61B 5/746* (2013.01)

(58) Field of Classification Search
CPC ... A61B 5/04012; A61B 5/0452; A61B 5/222; A61B 5/6869; A61N 1/3702
USPC ................................ 600/481, 509, 513, 519
See application file for complete search history.

(56) References Cited

U.S. PATENT DOCUMENTS

| | | | | |
|---|---|---|---|---|
| 4,718,427 A | * | 1/1988 | Russell | A61B 5/021 600/490 |
| 4,718,428 A | * | 1/1988 | Russell | A61B 5/021 600/490 |
| 4,873,980 A | | 10/1989 | Schaldach | |
| 5,427,112 A | * | 6/1995 | Noren | A61N 1/36585 600/512 |
| 5,549,650 A | * | 8/1996 | Bornzin | A61N 1/36542 607/24 |
| 5,609,612 A | | 3/1997 | Plicchi et al. | |
| 5,693,075 A | * | 12/1997 | Plicchi | A61N 1/365 600/515 |
| 7,242,983 B2 | | 7/2007 | Frei et al. | |
| 7,555,336 B2 | | 6/2009 | Sheth et al. | |
| 7,572,232 B2 | | 8/2009 | Li et al. | |
| 7,634,309 B2 | | 12/2009 | Wariar et al. | |
| 7,848,793 B1 | | 12/2010 | Shelchuk et al. | |
| 8,064,992 B2 | | 11/2011 | Henry et al. | |
| 8,428,698 B2 | * | 4/2013 | Keel | A61B 5/02416 600/509 |
| 8,452,404 B1 | | 5/2013 | Fischell et al. | |
| 8,483,828 B2 | | 7/2013 | Libbus et al. | |
| 8,494,629 B2 | * | 7/2013 | Makdissi | A61N 1/3627 607/17 |
| 8,571,655 B2 | | 10/2013 | Pastore et al. | |
| 8,718,765 B2 | * | 5/2014 | Baumann | A61B 5/02028 607/17 |
| 8,874,210 B2 | * | 10/2014 | Graindorge | A61N 1/365 600/513 |
| 8,938,286 B2 | * | 1/2015 | Dumont | A61B 5/7221 600/508 |
| 9,089,284 B2 | * | 7/2015 | Baumann | A61B 5/02028 |
| 2002/0016548 A1 | * | 2/2002 | Stadler | A61B 5/04011 600/509 |
| 2004/0176695 A1 | | 9/2004 | Poezevara | |
| 2004/0225332 A1 | * | 11/2004 | Gebhardt | A61N 1/3622 607/17 |
| 2004/0230249 A1 | | 11/2004 | Haefner | |
| 2006/0094967 A1 | * | 5/2006 | Bennett | A61B 5/0205 600/508 |
| 2006/0247701 A1 | * | 11/2006 | Zacouto | C12N 13/00 607/9 |
| 2007/0043299 A1 | | 2/2007 | Wariar et al. | |
| 2007/0167851 A1 | | 7/2007 | Vitali et al. | |
| 2007/0213773 A1 | * | 9/2007 | Hill | A61N 1/36114 607/3 |
| 2007/0239218 A1 | | 10/2007 | Carlson et al. | |
| 2007/0276453 A1 | * | 11/2007 | Hill | A61N 1/36114 607/62 |
| 2007/0293736 A1 | | 12/2007 | Casset | |
| 2008/0039904 A1 | * | 2/2008 | Bulkes | A61N 1/3622 607/62 |
| 2009/0192397 A1 | * | 7/2009 | Fischell | A61B 5/0031 600/516 |
| 2009/0209875 A1 | | 8/2009 | Giorgis et al. | |
| 2009/0216141 A1 | * | 8/2009 | Fischell | A61B 5/0031 600/509 |
| 2010/0023081 A1 | | 1/2010 | Audet et al. | |
| 2010/0087890 A1 | | 4/2010 | Wariar et al. | |
| 2010/0305647 A1 | | 12/2010 | McCabe et al. | |
| 2010/0318150 A1 | | 12/2010 | Graindorge | |
| 2011/0009714 A1 | | 1/2011 | Zong | |
| 2011/0066041 A1 | * | 3/2011 | Pandia | A61B 5/113 600/484 |
| 2011/0066042 A1 | * | 3/2011 | Pandia | A61B 5/029 600/484 |
| 2011/0098583 A1 | * | 4/2011 | Pandia | A61B 5/029 600/508 |
| 2011/0224748 A1 | * | 9/2011 | Lippert | A61B 5/02028 607/7 |
| 2011/0251656 A1 | | 10/2011 | Limousin | |
| 2012/0215089 A1 | * | 8/2012 | Fischell | A61B 5/0031 600/374 |
| 2012/0277546 A1 | * | 11/2012 | Soykan | A61B 5/0205 600/301 |
| 2013/0304144 A1 | | 11/2013 | Giorgis et al. | |
| 2014/0088442 A1 | * | 3/2014 | Soykan | B01D 61/243 600/483 |
| 2014/0107514 A1 | * | 4/2014 | Fischell | A61B 5/0031 600/523 |
| 2014/0148713 A1 | * | 5/2014 | Anselmi | A61N 1/3624 600/508 |
| 2014/0379040 A1 | | 12/2014 | Graindorge | |
| 2015/0190643 A1 | * | 7/2015 | McCabe | A61B 5/04001 607/19 |

FOREIGN PATENT DOCUMENTS

| | | |
|---|---|---|
| EP | 1 867 360 A2 | 12/2007 |
| EP | 2 092 885 A1 | 8/2009 |
| WO | WO-2009/107007 | 9/2009 |

\* cited by examiner

ACTIVE MEDICAL DEVICE FOR MONITORING THE STATUS OF A PATIENT SUFFERING FROM A RISK OF HEART FAILURE

CROSS REFERENCE TO RELATED APPLICATIONS

This application is a divisional of U.S. patent application Ser. No. 13/941,123, filed Jul. 12, 2013, which claims the benefit of and priority to French Patent Application No. 1256792, filed Jul. 13, 2012, both of which are hereby incorporated by reference herein in their entireties.

BACKGROUND

The present invention generally relates to "active implantable medical devices" as defined by the 14 Jun. 1993 Directive 93/41/EEC of the Council of the European Communities. This definition includes cardiac pacemakers, cardiac resynchronization therapy devices and/or implantable cardioverter defibrillators for treatment of rhythm disorders. The definition also includes active devices (e.g., implanted or not) and active devices for purely diagnostic systems. The definition includes external systems for home monitoring of patients (e.g., implementing a remote access device which is activated at regular intervals, such as daily, to download the data collected by an implant and to send the data for analysis to a remote station).

The invention also or alternatively relates to the monitoring of patients with heart failure, or at risk of heart failure. Heart failure is a complex disease with various causes and effects, notably including mitral valve regurgitation, dilated cardiomyopathy and ischemia. These are evolutionary and harmful phenomena; it is important to assess and monitor over time (e.g., to issue early warnings in case of worsening trend).

The change can result from a phenomenon called "cardiac remodelling," which can be defined as all heart changes in response to a disease and is usually associated with a worsening prognosis. This cardiac remodeling occurs over time by increasing the size of the left ventricle, with a worsening ejection fraction due to the decrease in contractility, and ultimately a decrease in cardiac output with serious consequences on the body by progression of heart failure.

With the help of alerts to worsening of the patient's condition, one can modify the configuration of a pacemaker. One example is to begin providing joint and permanent stimulation of the left and right ventricles to resynchronize the latter via a technique named CRT (Cardiac Resynchronization Therapy) or BVP (BiVentricular Pacing). Indeed, the beneficial effects provided by CRT therapy can lead, ultimately, to reassess the applied therapy and to again change the primitive configuration and setup of the resynchronizer.

The reference technique for the evaluation of the conditions listed above (valvular regurgitation, left ventricular dilatation, etc.) is the evaluation by echocardiography. This procedure traditionally must be carried out by a qualified practitioner and is traditionally time consuming and expensive, preventing the technique from being applied often.

Various techniques for automated monitoring and diagnosis have been proposed, including those presented in EP 1,867,360 A2 and its US counterpart US2007/0293736 (Sorin CRM S.A.S, previously known as ELA Medical), which offers cross various information from minute ventilation ("MV"), activity ("G" accelerometer), endocardial acceleration (EA) or intracardiac bioimpedance sensors. Analysis algorithms produce indicators of risk of cardiac decompensation, and cross analysis methods issue an early warning composite signal of preventive alert, on different levels, depending on the indicators produced by the algorithms.

U.S. 2007/043299 A1 describes a device implementing another technique, based on the cross-analysis of the peak-to-peak amplitude of the first peak of endocardial acceleration and of the heart rate, to assess the progress of heart failure in a patient implanted with the device.

These algorithms are effective in assessing the patient overall cardiac contractility and the more or less rapid deterioration of this contractility, corresponding to different levels of alert. However, they do not allow more specific assessment of the development or progression of certain specific pathologies such as those mentioned above (ischemia, regurgitation of the mitral valve, etc.). It would therefore be desirable to provide a device and method for monitoring and diagnosis which could be implemented in accordance with the patient's own condition (e.g., to deliver better or more specific alerts).

SUMMARY

Embodiments of the device may include means for measurement of the heart rate; means for collection of an endocardial acceleration signal; means for deriving, from the endocardial acceleration signal, a signal representative of the myocardial contractility; means for defining at least couples of values (e.g., a frequency/parameter pair) during successive cardiac cycles; classifier means for distribution of said couples of values in predetermined frequency classes of a discretized profile of values (e.g., frequency, parameter); and means for analysis of said profile, for delivering an index (a,b) representative of a clinical status of the patient.

The hemodynamic parameter may be representative of the myocardial contractility and is a temporal parameter representative of the time interval separating the first and the second peak of endocardial acceleration. The choice of this parameter is particularly advantageous for assessing the degree of ischemia of the patient and the specific evolution of this disease, regardless of the general evolution of his/her heart failure. Clinical studies have shown a significant change in the interval between the two peaks when a subsequent ischemic event to the occlusion of a coronary artery occurs.

Advantageously, embodiments of the device disclosed herein further include a method for collection of an endocardial acceleration signal. The device's method for delivering a hemodynamic parameter is configured to derive a hemodynamic parameter representative of the myocardium contractility from the endocardial acceleration signal.

The hemodynamic parameter representative of the myocardial contractility can be, for example, a peak-to-peak amplitude of the first peak of the endocardial acceleration parameter. The hemodynamic parameter representative of the myocardial contractility can also or alternatively be a temporal parameter representative of the time interval between the first and second peak of endocardial acceleration.

In one implementation, the analysis of the profile includes extraction of at least one representative data of the current profile of the patient, and of comparison of this representative current data to a predetermined reference representative data. The reference representative data can obtained from at least one prior profile of the patient, or be derived from values obtained from a known population of healthy patients. The analysis can include applying, before comparison with the reference representative data, a predetermined weighting to each profile class. The analysis may include modelling the current profile by linear regression or quadratic regression, the parameters of this regression forming said profile data.

In another implementation, the device further includes a component for discrimination of the phases of activity of the patient. The component may discriminate between three phases of patient activity (e.g., effort, rest and recovery). The acquisition methods define triplets of values (frequency, parameter, activity) over successive cardiac cycles, or series of successive cardiac cycles. The profile may be a discrete three-dimensional profile of values (frequency, parameter, activity). The classifier methods may place the triplets of values in classes of predetermined frequency of the three-dimensional profile.

An active medical device (e.g., an implantable stimulation resynchronization and/or defibrillation device, or a device for diagnostic purposes) may include:

means for measuring the heart rate (Fc);
means for collecting an endocardial acceleration signal (EA);
means able to derive from the endocardial acceleration signal an hemodynamic parameter representative of the myocardium contractility;
means of acquisition, for defining at least couples of values {frequency, parameter} during successive cardiac cycles, or of successive series of cardiac cycles;
classifier means (10) of distribution of said couples of values in classes of predetermined frequency of a discretized profile of values {frequency, parameter} (12); and
means (14) of analysis of said profile, able to deliver an index (a, b) representative of a patient's clinical status,
wherein said hemodynamic parameter representative of the myocardial contractility is a temporal parameter representative of the time interval (Ts) separating the first and the second peak of endocardial acceleration.

The means of analysis of the profile may be adapted to extract at least one data (a, b) representative of the current profile of the patient, and of comparison of this current data representative to a reference predetermined representative data. The reference representative data may be obtained from at least one previous patient profile. The reference representative data may be values collected from a known population of healthy patients. The analysis means may be further adapted, prior to the comparison to the reference representative data, to apply a predetermined weighting to each profile class. The analysis means may be adapted to model the current profile by a linear regression (RL) or a quadratic regression (RQ), the parameters of this regression forming said profile data (a,b).

The device may further include discriminator means for discriminating between activity phases of the patient (E, R, REC). The acquisition means may be adapted to define triplets of values {frequency, parameter, activity} during said successive cardiac cycles, or said series of successive cardiac cycles. The profile may be a three-dimensional profile of discretized values {frequency, parameter, activity}. The classifier means may be adapted to place said triplets of values in said predetermined frequency classes of said three-dimensional profile. The discriminated phases of patient activity may include phases of effort (E), of rest (R) and of recovery (REC).

Implementations of the device may include means for measuring the heart rate (HR). The device may further include means for delivering a hemodynamic parameter representative of the myocardial contractility, including the peak-to-peak amplitude (PEA1) of the first peak of endocardial acceleration, or the time interval between the first and second peak of endocardial acceleration. The device may further include means of acquisition, adapted to define at least pairs of values {frequency, parameter} during successive cardiac cycles, or successive series of cardiac cycles. The device may also include classifier means, adapted to distribute the pairs of values in predetermined frequency classes of a discretized profile of values {frequency, parameter} (12). The device may further include means of analysis of the profile, able to deliver an index (a, b) representative of a patient's clinical status.

An active medical device is configured to receive inputs and to calculate a hemodynamic parameter representative of myocardium contractility determined from an endocardial acceleration signal. The microcontroller acquires heart rate and hemodynamic parameter pairs of values during a plurality of cardiac cycles. The microcontroller is configured to distribute the pairs of values into discrete bins to develop a profile for analysis. The microcontroller is configured to conduct an analysis including calculating an index representative of the patient's clinical status. The hemodynamic parameter representative of the myocardial contractility is a time interval separating the first and the second peak of endocardial acceleration.

DETAILED DESCRIPTION

Figure 1:
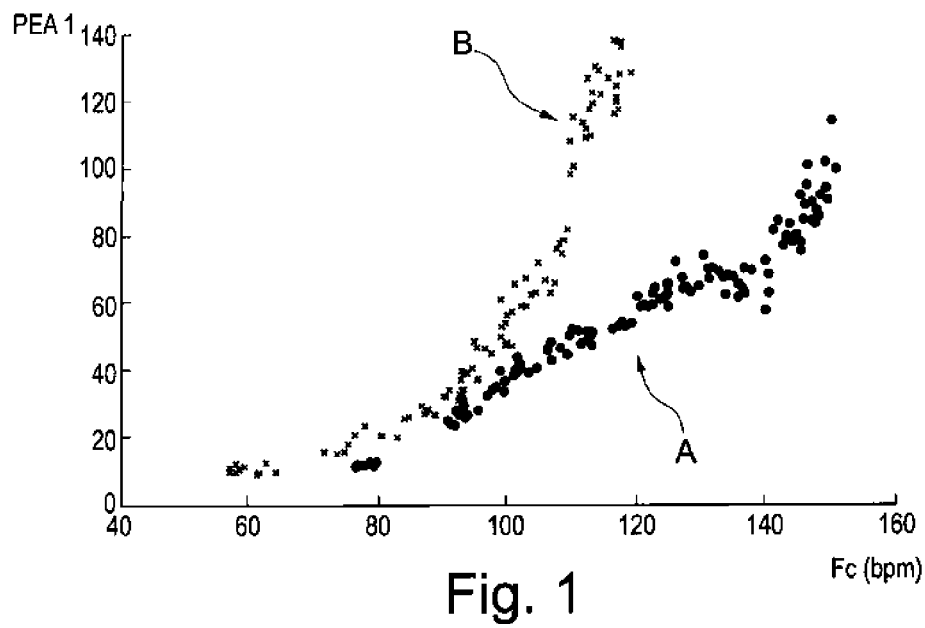
FIG. 1 shows a series of records showing the amplitude of the peak of endocardial acceleration according to the heart rate, before and after angioplasty, experimentally obtained for a patient suffering from mitral valve regurgitation.

As regards to its software aspects, the present invention can be implemented by an appropriate programming of the controlling software of a known device, for example, a cardiac pacemaker or a defibrillator/cardioverter. The device may be configured to collect a signal provided by endocardial leads and/or one or more implanted sensors.

The present invention may particularly be applied to implantable devices such as those of the Reply and Paradym device families produced and marketed by Sorin CRM, Clamart France, formerly known as ELA Medical, Montrouge, France. The present device may also be applied, for example, to external devices for in-home monitoring of the patient, such as the Smartview Remote Monitoring System, from Sorin CRM.

These devices include programmable microprocessor circuitry to receive, format, and process electrical signals collected (detected) by electrodes implanted and deliver stimulation pulses to these electrodes. The various analysis steps described herein may be partially or entirely performed by telemetry software stored in a memory of the implantable devices and executed to implement the functions of the invention described herein. The method of the invention is primarily implemented by software, using appropriate algorithms executed by a microcontroller or a digital signal processor.

The technique of the invention is based on the analysis of endocardial acceleration (hereinafter "EA"), which is a parameter that reflects phenomena contributing to myocardial mechanical function. EA can be measured by an accelerometer coupled to the heart muscle, as described for example in EP 0515319 A1 (Sorin Biomedica Cardio SpA). This document teaches a method for collecting an EA signal through an endocardial lead provided with a distal stimulation electrode implanted in the atrium or the ventricle and incorporating a microaccelerometer for measuring endocardial acceleration.

Although the present description refers to the analysis of an EA signal delivered by a sensor placed on an endocardial lead, the invention is also applicable to an EA signal obtained by other types of implantable sensors, such as a sensor of movement of a wall of the myocardium, an epicardial sensor or an accelerometer placed in the case of an implant. The invention is also applicable to the analysis of an external EA signal collected noninvasively (e.g., from a sensor attached to the patient's chest at the sternum).

The EA signal collected during a given cardiac cycle form two main components, corresponding to the two major heart sounds (sounds "S1" and "S2" of phonocardiogram); it is possible to recognize the following components in each cardiac cycle:

The EA1 component, beginning after the QRS complex, is produced by a combination of the closure of the atrio-ventricular valves, the opening of semilunar valves and the contraction of the left ventricle. The amplitude variations of this EA1 component are closely related to changes in the ventricular pressure (the maximum peak to peak amplitude being more precisely correlated to the positive maximum dP/dt pressure variation in the left ventricle) and may therefore be a parameter representative of the myocardial contractility, itself linked to the level of activity of the sympathetic system; and The EA2 component occurs during the isovolumetric ventricular relaxation. It accompanies the end of the ventricular systole and is mainly produced by the closure of aortic and pulmonary valves.

A number of other representative parameters may be calculated from the collected EA signal, including:

The peak-to-peak of the EA1 component, hereinafter "PEA1", that is to say the amplitude of the first peak of acceleration; and The time interval separating the component EA1 of the component EA2, hereinafter "Ts." This indicator which corresponds to the duration of the systole is generally counted between the moment marking the beginning of the EA1 component and the moment marking the beginning of the EA2 component.

EP 2092885 A1 (assigned to Sorin CRM S.A.S. previously known as ELA Medical) describes in detail techniques for analyzing an EA signal to, among other things, extract both PEA1 and Ts information. This document also describes a method by which these parameters may be determined, as well as other characteristics of the EA1 and EA2 components.

In FIG. 1, a series of records giving the value of PEA1 for heart rate Fc experimentally obtained for a patient with regurgitation of the mitral valve, before and after angioplasty, is shown. The A points correspond to records for a patient with severe regurgitation of the mitral valve, and the B crosses are those obtained for the same patient after an angioplasty procedure which allowed to absorb any regurgitation of the mitral valve. As can easily be seen, the gradient of the peak amplitude PEA1 versus heart rate Fc is much higher after the intervention (e.g., after the specific pathology has disappeared). This gradient and its modification are used to assess the patient's condition, as outlined below.

Figure 2:
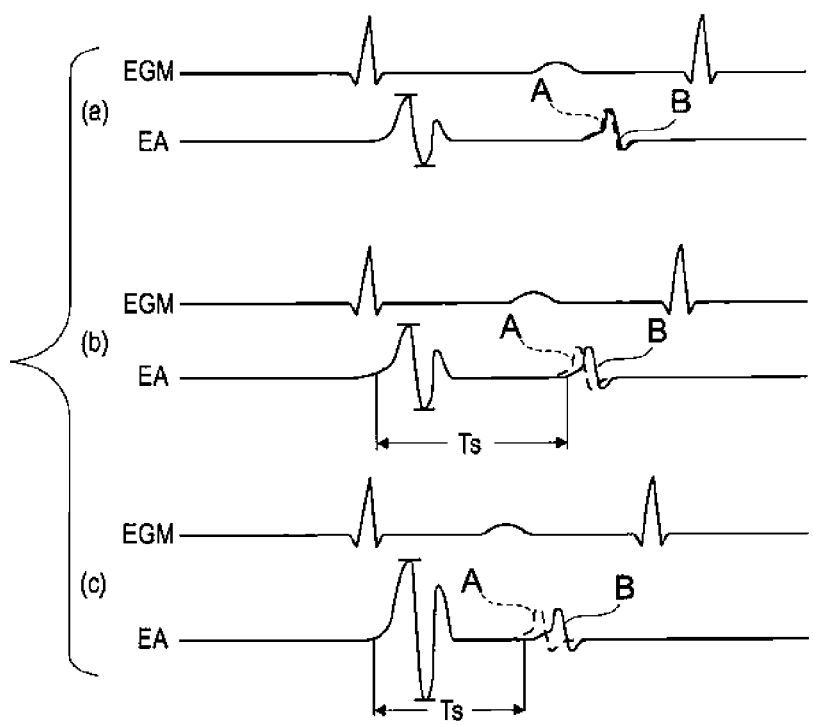
FIG. 2 shows various timing diagrams of electrogram (EGM) signals and endocardial acceleration (EA) signals experimentally identified on a healthy animal with progressive occlusion of a coronary artery.

FIG. 2 illustrates three timing diagrams of electrogram (EGM) and endocardial acceleration (EA) signals experimentally identified on a healthy animal, then with progressive occlusion of a coronary artery. The reduction, following the reduction in the flow of the coronary artery, of the time interval Ts separating the two EA1 and EA2 components is visible between the curve A (with reduced coronary flow) and the curve B (normal coronary flow). This observation may be used to assess the evolution of the patient in relation to increasing ischemia.

Figure 3:
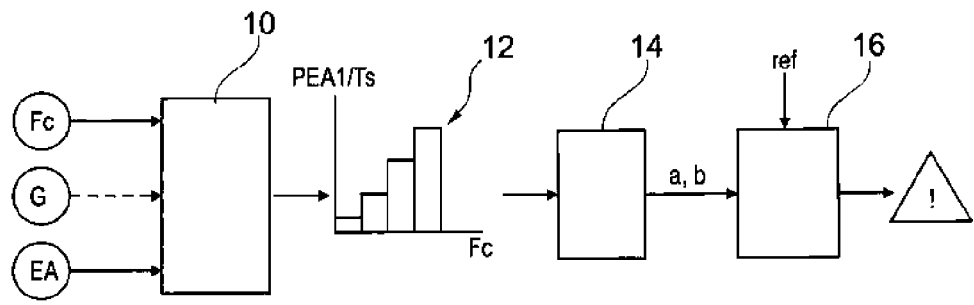
FIG. 3 is a schematic representation of the device of the invention, illustrating the sequence of the various stages of processing of the collected data.

FIG. 3 illustrates schematically the different steps of the processing according to an embodiment of the invention. The first step (block 10) is to collect signals with heart rate Fc, endocardial acceleration EA, and optionally patient activity G (by means of a sensor of a physical activity sensor, typically an accelerometer integrated in the implant). The data is processed to extract representative parameter values such as PEA1 and/or Ts. The data may be stored in a discrete profile 12 (e.g., having an appearance similar to that of an histogram) distributed over several classes, depending on the heart rate Fc.

The next step (block 14) includes performing an analysis of the profile 12 so as to derive one or more indices a, b . . . representative of the more or less altered state of the patient. These indices are then compared (at block 16) to reference values ref (e.g., so as to provide an alert, if necessary, in case of observed index worsening relative to the reference values). The basis of comparison ref can be either a previous state of the patient (e.g., relative and intrinsic comparison, compared with the same indices previously calculated for this patient) or reference values obtained for a known population of healthy patients (e.g., absolute comparison, by comparison to statistically and generally given criteria determined for a patient population).

Figure 4:
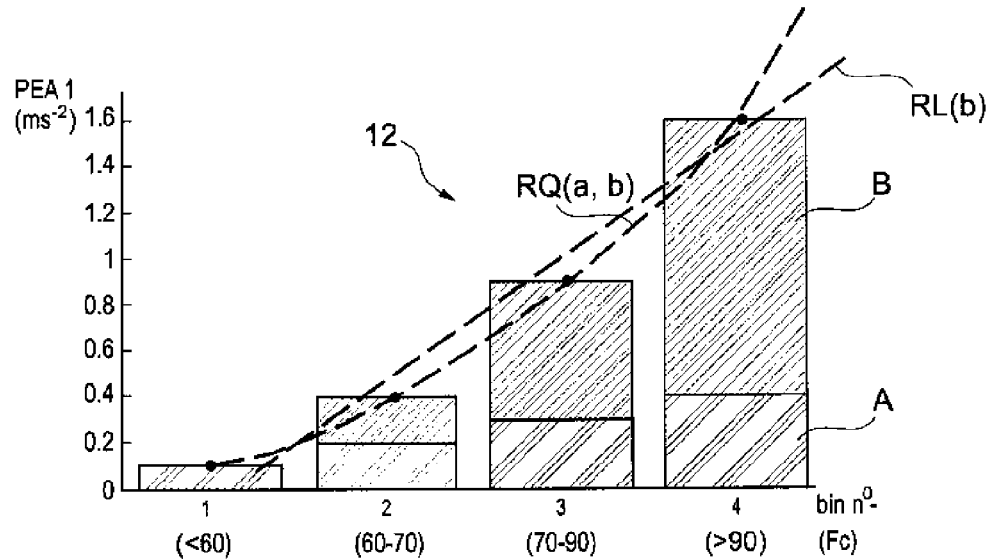
FIG. 4 is an example of a two-dimensional profile of the amplitude of the peak of the EA signal as a function of the heart rate, for a healthy patient and for a patient suffering from mitral valve regurgitation.
Figure 5:
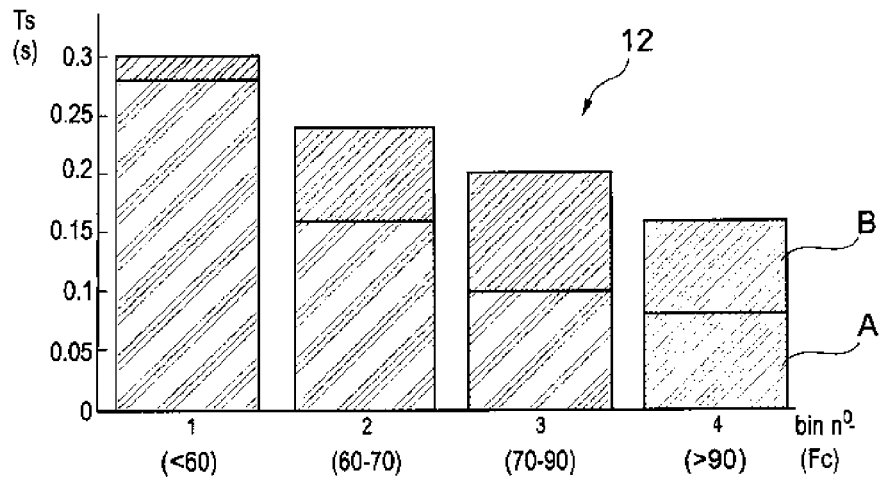
FIG. 5 illustrates an example of a two-dimensional profile providing the time interval separating the first peak of the second peak of the EA signal as a function of heart rate, for a healthy patient and for an ischemic patient.

FIGS. 4 and 5 more precisely show two examples of profiles 12 made from data collected by the device. The range of possible patient heart rate values is divided into several sub-heart rate ranges or "bins," which can either be determined in the same method for all patients, or tailored to specific values of patient base frequency and maximum frequency in sinus rhythm. These bins may be of equal width or not.

In the examples shown in FIGS. 4 and 5, a division of the heart rate range into four bins is made, corresponding to values of heart rate below 60 bpm, between 60 and 70 bpm, between 70 and 90 bpm, and greater than 90 bpm.

The current heart rate is continuously measured on the basis of the RR intervals. The adopted value Fc can advantageously be a weighted average heart rate of previous cycles, and/or previously calculated Fc values.

The characteristic parameters of the EA signal, namely PEA1 and/or Ts in the shown examples, are measured at each cycle and accumulated in one of the bins of the profile 12, depending on the corresponding Fc value. This combination of PEA1 and/or Ts parameters can take the form of a mean or median value, or be simply constituted by the sum of the values obtained, the corresponding number of involved cycles being known elsewhere.

The method of accumulation may be suspended for one or more cycles in case of occurrence of certain events, such as the detection of atrial extrasystole (ESA), of ventricular extrasystole (ESV) or of atrial or ventricular arrhythmia.

FIG. 4 more precisely shows the profile of the PEA1 parameter based of the heart rate Fc, classified on four heart rate bins. Two examples of profiles are shown, one A profile corresponding to a patient with regurgitation of the mitral valve, and the other B profile obtained for a healthy patient.

In FIG. 5, the evaluated parameter here is the duration Ts between the two peaks of endocardial acceleration, corresponding to the duration of systole. Two examples of profiles are shown, one A corresponding to an ischemic patient, and the other B obtained for a healthy patient. As discussed above, ischemic patients have a systolic period shorter than normal patients.

For a given patient the device may stores two profiles. The stored profiles may include a short-term profile based, for example, on records of the previous day or the previous two days. The stored profiles may further include a long-term profile based, for example, on the accumulation of the parameters collected during one month (alternatively, the long-term profile can be replaced by a reference profile obtained from a population of healthy patients).

The evaluation of the patient's condition is made by comparing the short-term profile and the long-term profile. This comparison can be performed by calculating and evaluating weighted values for each heart rate bin, e.g. 10% for bin 1 (<60 bpm), 20% for bin 2 (60-70 bpm), 30% for bin 3 (70 and 90 bpm) and 40% for bin 4 (>90 bpm). The algorithm calculates the difference between the long-term profile and the short-term profile for each bin and multiplies it by the weight associated with this bin, and then sums the values for all bins. An index representative of the difference between the long-term profile and the short-term profile is then obtained.

Another method to calculate such a representative index is to model each long-term and short-term profile, for example by linear regression RL of the form:

$$PEA1 = b.Fc + c$$

or by a quadratic regression RQ of the form:

$$PEA1 = a.Fc^2 + b.Fc + c$$

wherein b represents a linear gradient of the profile and, in the case of a quadratic regression, a indicates the curvature of the profile.

A high linear gradient b and a high quadratic coefficient a are indicative of a satisfactory condition of the patient. By comparing of the two short-term and long-term profiles, the evolution of the patient's condition can be evaluated:

An increase in the indices a or b of the short-term relative to the long term indicates an improvement in the patient's condition;

Comparable a and b indices between short-term and long term indicate stability of the status of the patient, and A reduction of the a or b indices of short-term versus the long-term shows a deteriorating condition of the patient.

In the latter case, an alert may be transmitted via a remote transmission to a doctor or exterior personnel. This alert can be generated by comparing the a and/or b indices with a given threshold, determined a priori from a known population of patients, or by a trend analysis of the short-term/long-term difference versus time. For example, an alert can be generated if the measured difference between the short-term profile and the long-term profile is negative for five consecutive days. These data can also be stored to be submitted to the doctor by electronic transmission or during an interrogation of the implant during a visit or hospital admission.

Figure 6:
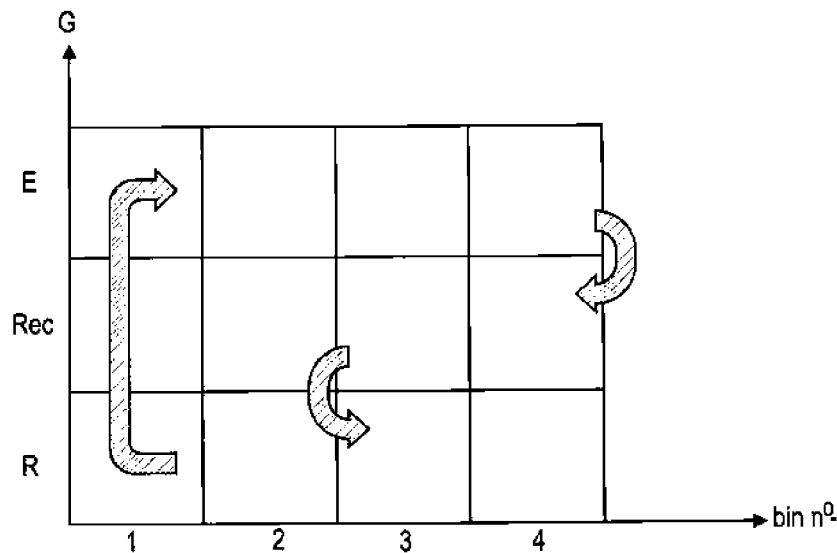
FIG. 6 is a diagram illustrating the introduction of a stress/rest/recovery criterion for further analysis, with the transitions between the different states.
Figure 7:
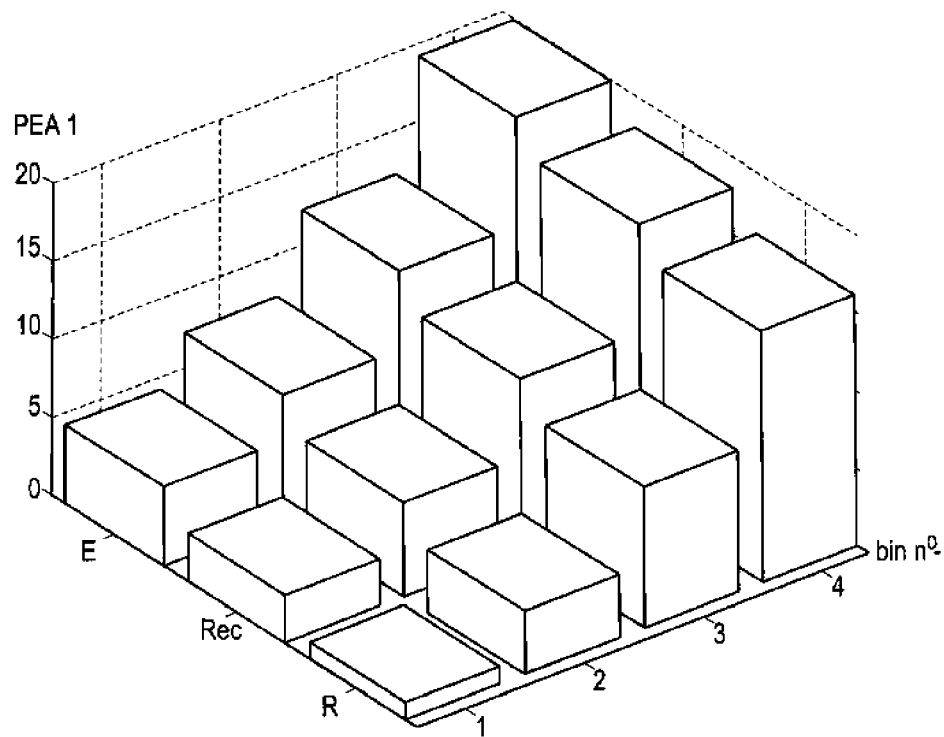
FIG. 7 is an example of three-dimensional profile providing the peak amplitude of the EA signal as a function of both heart rate and the activity state of the patient.

In the embodiments of FIGS. 6 and 7, the device considers a profile depending not only on heart rate Fc, but also on the activity status of the patient.

As shown in FIG. 6, for example, three sets of state activity, depending on the indication given by a sensor such as an accelerometer sensor (G sensor) integrated into the implant, are defined:

"Rest" R: low value of the activity sensor;
"Effort" E: high value of the activity sensor, and
"Recovery" REC: e.g. for a given fixed period after a period of "effort," and/or until the patient's heart rate decreases down to a specified resting frequency.

FIG. 6 shows e.g. the evolution of the patient's condition, following the arrows: starting from a stable rest situation and slow rhythm (bin1/R state), the patient begins to move (bin1/E state), which induces an increase in heart rate (up to bin4/E state). When the patient terminates his/her effort, he goes into recovery and the heart rate gradually decreases (bin4/REC state, then bin3/REC state). At the end of the required recovery time, the state becomes a resting state (bin3/R state) and the heart rate gradually decreases, still in the rest state until the base frequency corresponding to the initial situation (bin1/R state).

As shown in FIG. 7, a three-dimensional profile with 4×3 bins is defined, i.e. 4 frequency bins (as in FIG. 4) combined with 3 activity bins (activity/rest/recovery, labelled as E, R, Rec, respectively). The algorithm analyzes this three-dimensional profile and its short-term/long-term evolution using techniques similar to those described above for the two-dimensional profile of FIG. 4, in order to assess the evolution of the patient's pathology.

What is claimed is:

1. A computerized method for evaluating heart status of a patient, comprising:
    using a microcontroller coupled to heart rate and endocardial acceleration sensors to calculate a hemodynamic parameter;
    storing a plurality of heart rate and hemodynamic parameter pairs in bins, the bins grouped by heart rate, for both a long-term patient profile and a short-term patient profile;
    calculating a difference between the long-term profile and the short-term profile for each bin and multiplying each resultant difference by a weight for the bin;
    using the resulting products to calculate an index representative of the weighted difference between the long-term profile and the short-term profile; and generating an output from a device using a determination based on the index.

2. The computerized method of claim 1, wherein the hemodynamic parameter is the duration between two peaks of endocardial acceleration.

3. The computerized method of claim 1, wherein the hemodynamic parameter is the endocardial acceleration amplitude.

4. The computerized method of claim 1, wherein the determination based on the index comprises comparing the index to a threshold.

5. The computerized method of claim 4, wherein generating an output from the device comprises generating a graphical representation of a bar graph, wherein each heart rate bin forms a bar and each bar illustrates the long term profile data and the short term profile data for the bin.

6. The computerized method of claim 4, wherein generating an output comprises transmitting an alert from the device to a remote system.

7. The computerized method of claim 1, further comprising modelling the short-term profile using a linear regression model or a quadratic regression model.

8. The computerized method of claim 7, wherein parameters generated from the linear regression model or the quadratic regression model are used to calculate the index.

9. The computerized method of claim 1, wherein the bins grouped by heart rate are indicative of a discrimination between different activity phases of the patient.

10. The computerized method of claim 9, wherein the different activity phases of the patient include phases of effort, rest and recovery.

11. The computerized method of claim 9, further comprising defining triplets of values during different cardiac cycles, the triplets of values including a first value indicating an activity, as second value indicating the heart rate, and a third value indicating a time interval separating a first peak and a second peak of endocardial acceleration.

12. The computerized method of claim 11, further comprising developing a three dimensional graphical profile of the triplets, and placing the triplets in predetermined frequency classes of the three dimensional graphical profile.

13. The computerized method of claim 1, further comprising modifying a configuration of the device based on the index representative of the weighted difference between the long-term profile and the short-term profile.

14. A computerized method for evaluating heart status of a patient, comprising:
   tracking a plurality of heart rate, hemodynamic parameter, and activity triplets for a patient using sensor readings;
   grouping the tracked triplets into at least three heart rate bins spanning at least three activity level bins;
   comparing short term performance within each activity to long term performance within each activity level, wherein the comparison comprises evaluating the bin-to-bin hemodynamic parameter changes within each activity level; and
   transmitting an alert from a device to a remote system based on the index.

15. The computerized method of claim 14, wherein the comparison further comprises:
   multiplying a hemodynamic parameter assigned to a bin by a weighting value.

16. The computerized method of claim 15, wherein the comparison further comprises:
   calculating a difference between a long term performance and a short term performance for each heart rate bin and activity level bin pair.

17. The computerized method of claim 16, wherein the comparison further comprises:
   calculating an index representative of the difference between the long-term performance and the short-term performance.

18. The computerized method of claim 14, wherein the activity levels include levels of rest, effort and recovery.

19. The computerized method of claim 14, further comprising developing a three dimensional graphical profile of discrete values according to the tracked triplets, and placing the triplets in predetermined frequency classes of the three dimensional graphical profile.

* * * * *